United States Patent

Molteni et al.

[11] 4,125,616
[45] Nov. 14, 1978

[54] PYRIDOXYLIDINE AMINO BENZOATE COMPOUNDS

[75] Inventors: Luigi Molteni, Malnate, Varese, Italy; José A. Ramirez Fernandez, Madrid, Spain; Franco Scrollini, Voghera; Giampiero Vercesi, Rho, Milan, both of Italy

[73] Assignee: Zambeletti Espana, S.A., Madrid, Spain

[21] Appl. No.: 761,050

[22] Filed: Jan. 21, 1977

Related U.S. Application Data

[63] Continuation of Ser. No. 628,711, Nov. 4, 1975, abandoned.

[51] Int. Cl.² .................. A61K 31/44; A61K 31/525; C07D 213/10; C07D 413/12
[52] U.S. Cl. .................. 424/263; 424/248.55; 424/265; 542/423
[58] Field of Search .............. 260/240 G; 424/248.55, 424/263, 267; 542/423

[56] References Cited

U.S. PATENT DOCUMENTS

| | | | |
|---|---|---|---|
| 2,614,104 | 10/1952 | Winsten | 260/240 G |
| 3,551,478 | 12/1970 | Schmitt et al. | 424/267 |
| 3,632,806 | 1/1972 | Okumura et al. | 260/240 G |

FOREIGN PATENT DOCUMENTS 1,263,155  2/1972  United Kingdom.

OTHER PUBLICATIONS

Iwanami et al., Bull. Chem. Soc. Japan 41(1968), pp. 161–165.
Zennu et al., Chem. Abst. 73(1970), #87798.

*Primary Examiner*—Allen B. Curtis
*Attorney, Agent, or Firm*—Ladas, Parry, Von Gehr, Goldsmith & Deschamps

[57] ABSTRACT

Pyridoxin derivatives of the general formula:

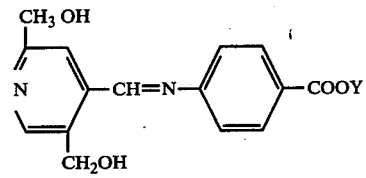

wherein Y is described herein for use as antineuritics and analgesic drugs.

3 Claims, No Drawings

PYRIDOXYLIDINE AMINO BENZOATE COMPOUNDS

This is a continuation of application Ser. No. 628,711 filed Nov. 4, 1975, now abandoned.

The present invention refers to products for the synthesis between pyridoxal and basic esters of p-aminobenzoic acid of the general formula:

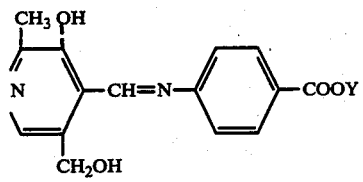

wherein Y represents a

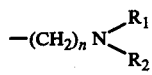

group wherein $n = 2$ or 3, while $R_1$ and $R_2$, which can be equal or different, represent alkyl residues having from 1 to 5 carbon atoms, either straight or branched chain, or cycloalkyl residues with 5 or 6 members or joined to the nitrogen atom form a ring with 5 or 6 members which, eventually, comprises other heteroatoms.

The invention refers, furthermore, to non-toxic salts of the products of formula (I) with organic and inorganic acids.

Finally, the object of the invention is to proportion a process for preparing the compounds of formula (I).

The compounds, according to the invention, have certain characteristics such as those which permit them to be advantageously used in human therapy, as drugs having a vitamin $B_6$ type action. In fact they are stable, and prove to have an unmistakable pharmacological effect through the following administration means: oral, intramuscular and endovenous; the pharmacological effect, besides being of the vitamin $B_6$ type, has, due to some reserve substances, a reliable analgesic effect, a highly-valued property for a vitamin $B_6$ in its frequent uses as an antineuritic drug.

The activity and microbiological merit of the compounds of the invention have been determined according to the methodology of ATKIN L. etc. - 1943, Ind. Eng. Chem. (Anal. Edition) 15, 141-144, using as the increase in the growth of the Saccharomyces Carlsbergensis ATCC 1080, gradual doses of the new substances in comparison with the Pyridoxin HCl Reference Standard.

The pharamacological activity of the products, object of the invention, has been demonstrated in the rat fed with a diet lacking vitamin B according to the methodology of MIRONE L. and JACKSON C. D. J. of Nutrition, 167, 67, 1959.

All the tested compounds have demonstrated a vitamin $B_6$ type activity, molary comparable with that of the vitamin $B_6$ Reference Standard.

The search for the analgesic potency, according to the methodology of Wolfe G., Mc. Donald A. D., J. Pharmacol, Exptl. Therap., 80, 300, 1944, modified by Eddy N. B., Leimbach D., J. Pharmacol, Explt. Therap. 107, 385, 1953, has demonstrated for some of them an interesting analgesic activity; the most active compounds, from this point of view, are: pyrrolidin-ethyl pyridoxylidene-aminobenzoate hydrochloride, morpholin-ethyl pyridoxylidene-aminobenzoate hydrochloride, and diethyl-amino-ethyl pyridoxylideneaminobenzoate hydrochloride.

Furthermore, the latter two have demonstrated, in a statistically significant manner, to potentiate analgesic substances having central activity (such as propoxyphene, codeine, etc.).

The acute and chronic modest toxicity of the compounds object of the invention, and their noteworthy interesting pharmacological charactefistics, justify their use in human therapy as substances having an action of the vitamin $B_6$ type, furthermore empowered with analgesic potency.

According to the invention, the compounds of formula (I) are obtained by the reaction of pyridoxal with the basic esters of p-amino-benzoic acid, by elimination of one molecule of water and subsequent formation of a Schiff base, according to the scheme:

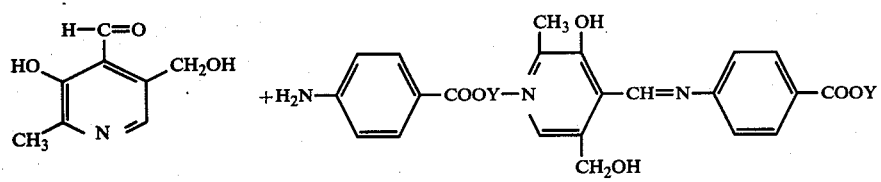

wherein Y is as defined above.

Synthesis is carried out normally between the pyridoxal hydrochloride and the basic esters of p-aminobenzoic acid, under anhydrous conditions and in a polar anhydrous solvent (generally methyl or ethyl alcohol or a mixture of both), at a temperature comprised between $-10°$ C and $+70°$ C.

As a complement of the reaction, the Schiff base obtained crystallizes directly from the reaction solvent without the need, for the majority of the products, of concentrations or special artifices. The products, obtained according to the above illustrated scheme, have been readily isolated to the state of chemical purity (as bases or monohydrochlorides) as white or yellow crystalline substances or as yellowish-orange hygroscopic amorphous powders.

The following examples will illustrate the process according to the invention.

EXAMPLE I 14.9 g. of pyridoxal hydrochloride were added, at room temperature and under anhydrous conditions, to the solution of 17.32 g. of diethyl-aminoethyl p-aminobenzoate in 318 ml. of absolute ethanol and 12 ml. of methanol.

By stirring, an intensely yellow solution was obtained in a very short period of time. The reaction was completed at +37° C in a thermostatic chamber, under a nitrogen current for 24 hours.

As the reaction proceeded, the Schiff base crystallized in the form of a solid white, somewhat yellowish, hydrochloride. After filtration and washing with anhydrous ether of the crystalline product obtained, 18 g. of diethyl-amino-ethyl pyridoxylidene-aminobenzoate hydrochloride were obtained, melting point 178°–180° C.

The centesimal analysis for C, H, N, Cl gave the following values:

|    | Calculated | Found  |
|----|-----------|--------|
| C  | 59.78%    | 60.10% |
| H  | 6.69%     | 6.70%  |
| N  | 9.96%     | 9.70%  |
| Cl | 8.40%     | 8.30%  | according to the formula: $C_{21}H_{27}N_3O_4 \cdot HCl$

An eventual crystallization of absolute methanol did not modify such analysis nor the melting point.

EXAMPLE II

A solution of 0.012 mole (2.83 g) of diethyl-amino-ethyl p-aminobenzoate in 4 ml. of absolute ethanol + 1 ml. of absolute methanol was added to the suspension of 0.05 mole (2 g) of pyridoxal hydrochloride in 15 ml. of absolute alcohol.

The yellow mass, formed immediately, was placed in a thermostatic chamber at +4° C for 48 hours, after which period of time it had been converted into a white crystalline mass which, collected and dried after an eventual wash with anhydrous ethyl ether, weighed 2.5 g.

The product crystallized in absolute methanol weighed 2.2 g. and had a melting point of 178°–180° C and the following elemental analysis:

|    | Calculated | Found  |
|----|-----------|--------|
| C  | 58.78%    | 60.50% |
| H  | 6.69%     | 6.75%  |
| N  | 9.96%     | 9.75%  |
| Cl | 8.40%     | 8.30%  | according to the formula: $C_{21}H_{27}N_3O_4 \cdot HCl$.

EXAMPLE III 2 g. of pyridoxal hydrochloride were dissolved in 20 ml. of $H_2O$ and, separately, 2.72 g. of diethyl-amino-ethyl p-aminobenzoate hydrochloride in 100 ml. of 1N HCl.

The two solutions joined at room temperature had an intense yellow colour.

The reaction was always completed at room temperature, by stirring for 6 hours.

By alkalinization with 10% NaOH under cooling, a solid yellowish-orange mass was obtained which, filtered, washed with frozen $H_2O$ and dried over $P_2O_5$, weighed 2 g.

By crystallization of the benzol, 1.5 g. of base diethyl-amino-ethyl pyridoxylidenebenzoate were obtained, melting point 115°–117° C.

The elemental analysis gave the following results:

|   | Calculated | Found  |
|---|-----------|--------|
| C | 65.43%    | 65.10% |
| H | 7.06%     | 6.99%  |

|   | Calculated | Found  |
|---|-----------|--------|
| N | 10.90%    | 10.70% | according to the formula: $C_{21}H_{27}N_3O_4$.

EXAMPLE IV

Following the procedure of Example 1, using 11.01 g. of n-di-butyl-amino-propyl p-aminobenzoate and 6.09 g. of pyridoxal hydrochloride, 9.6 g. of n-di-butyl-amino-propyl pyridoxylideneaminobenzoate hydrochloride were obtained.

Whitish-pink crystals, melting point 161°–163° C.

The centesimal analysis for C, H, N, Cl gave the following values:

|    | Calculated | Found  |
|----|-----------|--------|
| C  | 63.46%    | 63.26% |
| H  | 7.78%     | 7.68%  |
| N  | 8.54%     | 8.52%  |
| Cl | 7.20%     | 7.10%  | according to the formula: $C_{26}H_{37}N_3O_4 \cdot HCl$.

EXAMPLE V 9.5 g of iso-dipropyl-amino-ethyl p-amino-benzoate and 6.09 g. of pyridoxal hydrochloride were added under anhydrous conditions to 90 ml. of absolute ethanol.

The mass was heated under stirring at 40° for 10 minutes, until an intensely yellow solution was obtained, which was then left at room temperature for 24 hours, under stirring.

A white, somewhat yellowish, solid was obtained by crystallization, as the reaction proceeded, which was, once cooled, filtered and washed with cold methanol and with anhydrous ether.

9 g. of iso-di-propyl-amino-ethyl pyridoxilideneaminobenzoate hydrochloride were obtained, having a melting point of 125°–127° C.

The centesimal analysis for C, H, N, Cl gave the following values:

|    | Calculated | Found  |
|----|-----------|--------|
| C  | 61.38%    | 61.28% |
| H  | 7.17%     | 7.07%  |
| N  | 9.34%     | 9.32%  |
| Cl | 7.88%     | 7.80%  | according to the formula $C_{23}H_{31}N_3O_4 \cdot HCl$.

EXAMPLE VI 8.12 g. of pyridoxal hydrochloride were suspended under stirring in 100 cc. of absolute ethanol. The temperature was raised to 40° C and the solution of 12.00 g. of di-ethyl-amino-propyl p-aminobenzoate was added slowly, dropwise, and under stirring to 100 cc. of absolute ethanol. The temperature was maintained at 40° C for 20 minutes until a yellowish-straw coloured solution was obtained which was left under stirring for 48 hours, protected from the light; it was cooled to +4° C and a solid crystalline was collected which was washed with acetone and when dry weighed 12 g.

The di-ethyl-amino-propyl pyridoxylideneaminobenzoate hydrochloride had a melting point of 165°–167° C.

The centesimal analysis for C, H, N, Cl gave the following values:

|    | Calculated | Found  |
|----|------------|--------|
| C  | 60.60%     | 60.30% |
| H  | 6.93%      | 6.91%  |
| N  | 9.64%      | 9.62%  |
| Cl | 8.13%      | 8.03%  | according to the formula: $C_{22}H_{29}N_3O_4 \cdot HCl$.

EXAMPLE VII

Following the procedure of Example V, using 3.50 g. of n-dibutyl-amino-ethyl p-aminobenzoate and 2.03 g. of pyridoxal hydrochloride, 1.00 g. of n-di-butyl-amino-ethyl pyridoxylideneaminobenzoate was obtained, a yellowish-white crystalline powder with a melting point of 147°–148° C.

The centesimal analysis for C, H, N, Cl gave the following values:

|    | Calculated | Found  |
|----|------------|--------|
| C  | 62.81%     | 62.80% |
| H  | 7.59%      | 7.60%  |
| N  | 8.79%      | 8.80%  |
| Cl | 7.42%      | 7.43%  | according to the formula: $C_{25}H_{35}N_3O_4 \cdot HCl$.

EXAMPLE VIII

Following the procedure of Example VI, 8.12 g. of pyridoxal hydrochloride were reacted with 11.2 g. of pyrrolidin-ethyl p-aminobenzoate. 10.5 g. of pyrrolidin-ethyl pyridoxylideneaminobenzoate hydrochloride were obtained.

A white crystalline powder, melting point 149°–150° C.

The centesimal analysis for C, H, N, Cl gave the following values:

|    | Calculated | Found  |
|----|------------|--------|
| C  | 60.06%     | 60.02% |
| H  | 6.24%      | 6.23%  |
| N  | 10.00%     | 10.01% |
| Cl | 8.44%      | 8.42%  | according to the formula: $C_{21}H_{25}N_3O_4 \cdot HCl$.

EXAMPLE IX

To the solution of 3.00 g. of morpholinethyl p-aminobenozate in 50 cc. of absolute methanol, were added 2.03 g. of pyridoxal hydrochloride at 40° C with stirring.

An orangy solution was obtained in a short period of time. The reaction was left to complete for 48 hours at room temperature and in no case higher than 30° C, protected from the light and with stirring.

It was dry concentrated under vacuum, not exceeding 30° C. It was again collected with acetone and dry-concentrated. This operation was repeated three times.

Petroleum ether was added with stirring and a yellow precipitate was obtained which was washed over the filter with anhydrous ether.

The morpholin-ethyl pyridoxylideneaminobenzoate hydrochloride, 1.00 g. was hygroscopic.

The centesimal analysis gave the following values:

|    | Calculated | Found  |
|----|------------|--------|
| C  | 57.86%     | 57.85% |
| H  | 6.01%      | 6.01%  |
| N  | 9.64%      | 9.62%  |
| Cl | 8.13%      | 8.12%  | according to the formula: $C_{21}H_{25}N_3O_5 \cdot HCl$.

EXAMPLE X

Following the procedure of Example IX, using 3.50 g. of iso-di-butyl-amino-ethyl p-aminobenzoate and 2.03 g. of pyridoxal hydrochloride, 0.9 g. of iso-di-butyl-amino-ethyl pyridoxylideneaminobenzoate hydrochloride were obtained.

A yellowish-orange hygroscopic powder.

The centesimal analysis for C, H, N, Cl gave the following values:

|    | Calculated | Found  |
|----|------------|--------|
| C  | 62.81%     | 62.80% |
| H  | 7.59%      | 7.60%  |
| N  | 8.79%      | 8.80%  |
| Cl | 7.42%      | 7.43%  | according to the formula: $C_{25}H_{35}N_3O_4 \cdot HCl$.

EXAMPLE XI

Following the procedure of Example IX, using 3.15 g. of piperidin-propyl p-aminobenzoate and 2.03 g. of pyridoxal hydrochloride, 1.10 g. of piperidin propyl pyridoxylideneaminobenozate hydrochloride were obtained as a yellow hygroscopic powder.

The centesimal analysis for C, H, N, Cl gave the following values:

|    | Calculated | Found  |
|----|------------|--------|
| C  | 61.66%     | 61.65% |
| H  | 6.75%      | 6.73%  |
| N  | 9.38%      | 9.35%  |
| Cl | 7.91%      | 7.89%  | according to the formula: $C_{23}H_{29}N_3O_4 \cdot HCl$.

EXAMPLE XII

Following the procedure of Example IX, using 2.98 g. of piperidin-ethyl p-aminobenozate and 2.03 g. of pyridoxal hydrochloride, 0.9 g. of piperidin-ethyl p-aminobenzoate hydrochloride were obtained as a yellow-orange hygroscopic powder.

The centesimal analysis for C, H, N, Cl gave the following values:

|    | Calculated | Found  |
|----|------------|--------|
| C  | 60.89%     | 60.87% |
| H  | 6.50%      | 6.51%  |
| N  | 9.68%      | 9.66%  |
| Cl | 8.17%      | 8.18%  | according to the formula: $C_{22}H_{27}N_3O_4 \cdot HCl$

EXAMPLE XIII

Following the procedure of Example IX, using 2.70 g. of di-methyl-amino-propyl p-aminobenzoate and 2.03 g. of pyridoxal hydrochloride, 0.80 g. of di-methyl-amino-propyl pyridoxylideneaminobenzoate hydrochloride were obtained, as a yellow hygroscopic powder.

The centesimal analysis for C, H, N, Cl gave the following values:

|   | Calculated | Found |
|---|---|---|
| C | 58.89% | 58.87% |
| H | 6.42% | 6.41% |
| N | 10.32% | 10.30% |
| Cl | 8.69% | 8.70% | according to the formula: $C_{20}H_{25}N_3O_4 \cdot HCl$.

We claim:

1. Pyridoxin derivatives of the general formula I:

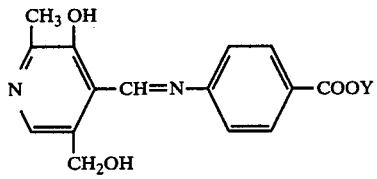 (I)

wherein Y represents a

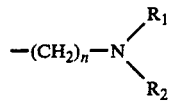

group wherein $n = 2$ or 3, while $R_1$ and $R_2$, which can be equal or different, represent alkyl groups having from 1 to 5 carbon atoms either straight or branched chain, or cycloalkyl residues with 5 or 6 members or joined to the nitrogen atom form a ring with 5 or 6 members which optionally comprise one oxygen atom, and their non-toxic salts with organic and inorganic acids.

2. Di-ethyl-amino-ethyl pyridoxylidene aminobenzoate HCl.

3. A pharmaceutical composition for use as an antineuritic and analgesic drug comprising as active principle the compound of claim 2, in association with a pharmaceutically acceptable carrier, the amount of the active principle being effective for use as an antineuritic or analgesic drug.

* * * * *